US008067225B2

(12) United States Patent
Fernández Sevilla et al.

(10) Patent No.: US 8,067,225 B2
(45) Date of Patent: Nov. 29, 2011

(54) MICROALGA SPECIES AND ITS APPLICATION FOR ANIMAL, HUMAN CONSUMPTION AND IN OBTAINING CAROTENOIDS

(75) Inventors: José Maria Fernández Sevilla, Almeria (ES); Emilio Molina Grima, Almeria (ES); Jerónimo J. Pérez Parra, El Ejido (ES); Francisco Gabriel Acien Fernández, Aguadulce (ES); Juan José Mágan Cañadas, Almeria (ES); Thomas Friedl, Goettingen (DE)

(73) Assignees: Universidad de Almeria, Almeria (ES); Caja Rural Intermediterranea, Almeria (ES)

( * ) Notice: Subject to any disclaimer, the term of this patent is extended or adjusted under 35 U.S.C. 154(b) by 809 days.

(21) Appl. No.: 11/816,614

(22) PCT Filed: Feb. 17, 2006

(86) PCT No.: PCT/ES2006/000072
§ 371 (c)(1),
(2), (4) Date: May 21, 2008

(87) PCT Pub. No.: WO2006/087405
PCT Pub. Date: Aug. 24, 2006

(65) Prior Publication Data
US 2009/0117223 A1 May 7, 2009

(30) Foreign Application Priority Data
Feb. 18, 2005 (ES) .................................. 200500374

(51) Int. Cl.
*C12N 1/12* (2006.01)

(52) U.S. Cl. ..... 435/257.5; 435/67; 435/134; 435/257.1

(58) Field of Classification Search ........................ None
See application file for complete search history.

(56) References Cited

FOREIGN PATENT DOCUMENTS
DE  40 18 820 A1  12/1991
GB  1157135  7/1969
GB  1318463  5/1973

OTHER PUBLICATIONS

Grima et al., Biotechnology Advances, 2003, vol. 20, p. 491-515.*
Tukaj et al. "Changes in the pigment patterns and the photosynthetic activity during a light-induced cell cycle of the green alga *Scenedesmus armatus*." Plant Physiology and Biochemistry vol. 41. 2003. pp. 337-344.
Deventer et al. "Effects of prolonged darkness on the relative pigment content of cultured diatoms and green algae." *Aquatic Sciences* vol. 58. No. 3. 1996. pp. 241-252.
Krasnovska et al. "Pigment composition of six xanthophycean algae and *Scenedesmus quadricauda*" Biologia Bratislava vol. 49. No. 4. 1994. pp. 501-509.
Retracted: Belarbi et al. "A process for high yield and scaleable recovery of high purity eicosapentaenoic acid esters from microalgae and fish oil." *Process Biochemistry.* vol. 35. 2000. pp. 951-969.
Belarbi et al. "A process for high yield and scaleable recovery of high purity eicosapentaenoic acid esters from microalgae and fish oil." *Enzyme and Microbial Technology.* vol. 26. 2000. pp. 516-529.
Borowitzka et al. "Commercial production of microalgae: ponds, tanks, tubes and fermenters." *J. of BioTech.* vol. 70. 1999. pp. 313-321.
Del Campo et al. "Lutein production by *Muriellopsis* sp. in an outdoor tubular photobioreactor." *J. of BioTech.* vol. 85. 2001. pp. 289-295.
Molina Grima et al. "The Production of Polyunsaturated Fatty Acids by Microalgae: from Strain Selection to Product Purification." *Process Biochem.* vol. 30. No. 8 1995. pp. 711-719.
Guerin et al. "*Haematococcus astaxanthin*: applications for human health and nutrition." *TRENDS.* vol. 21. No. 5. 2003. pp. 210-216.
Morist et al. "Recovery and treatment of *Spirulina platensis* cells cultured in a continuous photobioreactor to be used as food." *Process Biochem.* vol. 37. 2001. pp. 535-547.

* cited by examiner

*Primary Examiner* — Kade Ariani
(74) *Attorney, Agent, or Firm* — Merchant & Gould P.C.

(57) ABSTRACT

The invention relates to a novel microalga species and to the use thereof for animal and/or human consumption and in the production of carotenoids. A novel strain of *Scenedesmus* has been isolated at the Las Palmerillas experimental station, Cajamar, identified as microorganisms that had not been previously registered by the University of Gottinghem and deposited within the Culture Collection of Alagae and Protozoa (CCAP) as *Scenedesmus almeriensis*. The novel strain, which can be used for animal and/or human consumption, produces large quantities of carotenoids, particularly lutein and beta-carotene. *Scenedesmus almeriensis* grows adequately in a wide range of temperatures from 10° C. to 40° C. at a pH of between 7 and 9.5 and can tolerate high concentrations of copper, up to 1 mg/L. The microalgal strain is grown in a 4000 L photobioreactor, into which the culture is inserted mechanically, and produces less than 4 mg of lutein per gram of dry material. Said strain is suitable for the production of carotenoids that can be used in the treatment of ocular macular disorders.

9 Claims, 1 Drawing Sheet

MICROALGA SPECIES AND ITS APPLICATION FOR ANIMAL, HUMAN CONSUMPTION AND IN OBTAINING CAROTENOIDS

This application is the U.S. national stage application of International Application No. PCT/ES2006/000072 filed on Feb. 17, 2006, published as WO 2006/087405, which claims priority to Spain Application No. P200600374, filed on Feb. 18, 2005. The disclosure of the priority application is incorporated by reference in its entirety.

OBJECT OF THE INVENTION

The present invention relates to a new microalga species, isolated and verified as a new species not previously described, having important applications for both aquaculture and for human consumption, and even in obtaining carotenoids or carotenoid extracts for animal and/or human use.

The microalga is a species of the *Scenedesmus* genus registered as *Scenedesmus almeriensis* and deposited within the legally recognized official collection (Culture Collection of Algae and Protozoa, CCAP, SAMS Research Services Ltd., Scottish Marine Institute, OBAN, Argyll PA37 1QA, Scotland, United Kingdom: Deposit No. 276/24; Date of deposit: Feb. 16, 2005). An electron microscope image of this microalga is shown in FIG. 1. This microalga is characterized by a high growth rate, of 0.08 $h^{-1}$, high tolerance to wide temperature ranges, from 10° C. to 40° C., and a high carotenoid content, especially lutein.

BACKGROUND OF THE INVENTION

There are thousands of catalogued microalga species, although only a few of them are commercially exploited. The main requirements a microalga species must meet to be susceptible of industrial use are suitable growth and a different biochemical composition conferring it the highest possible added value. In this sense, the microalga species that are commercially exploited today range from *Chlorella* and *Nannochloropsis* for aquaculture (Borowitzka, Journal of Biotechnology, 70(1-3), (1999) 313-321) to *Spirulina* for human consumption (Morist et al., Process Biochemistry, 37(5), (2001), 535-547), or *Dunaliella* and *Haematococcus* for the production of carotenoids such as beta-carotene and astaxanthin, respectively (Guerin et al., Trends in Biotechnology, 21(5), (2003) 210-216).

Although many other species have been described as potentially interesting because of their valuable biochemical profile, their low growth rate or the difficulty of producing them due to stress sensitivity and/or easy contamination have prevented said commercial exploitation. This is the case of the microalgae *Isochrysis galbana* (Molina et al., Process Biochemistry, 30(8), (1995) 711-719) or *Monodus Subterraneous* (Belarbi et al., Process Biochemistry, 35(9), (2000) 951-969). In relation to the production of lutein, the microalga *Muriellopsis* sp. has been adequately grown in small, 50 L, laboratory scale tubular photobioreactors with production capacities of up to 180 mg lutein/$m^2$/day, although the photosynthetic efficiency is very low, 4% (José A. Del Campo et al., Journal of Biotechnology 85 (2001) 289-295). The results obtained with the new isolated strain double said production capacity, pending optimization.

DESCRIPTION OF THE INVENTION

The present invention presents a new microalga species characterized by a high growth rate and high tolerance to extreme cultivation conditions, further having a very uncommon carotenoid content, therefore it is a useful source for obtaining both biomass and these carotenoids, and especially lutein, in any of their forms.

The microalga *Scenedesmus almeriensis* object of the present invention is characterized by growth rates of up to 0.08 l/h, tolerance to wide pH ranges (between 7.0 and 9.5) and temperature ranges (between 10° C. and 40° C.) and high lutein contents, of up to 0.5% of the dry weight of the biomass. The most suitable conditions for the growth of the microalga *Scenedesmus almeriensis* are a temperature of 30° C., a pH of 8.0, and without the addition of vitamins. The microalga *Scenedesmus almeriensis* can further grow in a large variety of culture mediums, a suitable growth having been determined in the nutritive solutions used in intensive agriculture under plastic. According to the observations under electron microscope carried out, said microalga has a very resistant cell wall protecting it against mechanical stress phenomena, thus withstanding its propulsion by means of centrifugal pumps of up to 2.0 HP of power.

The microalga *Scenedesmus almeriensis* is further characterized by a high photosynthetic efficiency, reaching values of 12% in its large scale cultivation in tubular reactors 4000 L in volume installed in a greenhouse. The maximum biomass production capacity obtained under these conditions was 0.8 g/L/day. However, the most interesting data is its high lutein production capacity, which reached maximum values of 480 mg lutein/$m^2$/day. Said values were obtained by means of continuous cultivation, this being the best way to produce this microalga. By operating in this way, a high-quality, homogenous biomass is obtained with a biochemical profile that is very suitable for its use in nourishing fish hatchlings and mollusk larvae, nourishing animals and livestock, as a dietary supplement and in human nutrition, in obtaining oils rich in poly-unsaturated fatty acids and carotenoids, and especially for obtaining oils rich in lutein, with up to 30% by weight of lutein.

The microalga *Scenedesmus almeriensis* has been grown under controlled pH and temperature conditions with values of 8.0 and 30° C., respectively, in 4000 L tubular reactors, obtaining a high-quality homogenous biomass with a high lutein content of up to 0.5% of the dry biomass. This biomass is susceptible of being used in obtaining extracts or oils rich in lutein. Therefore, oils rich in lutein with up to 50% by weight of lutein have been obtained by means of chemical methods. These extracts are potentially useful for human consumption in the prevention and treatment of different disorders, particularly those related to senile macular degeneration.

Figure 1:
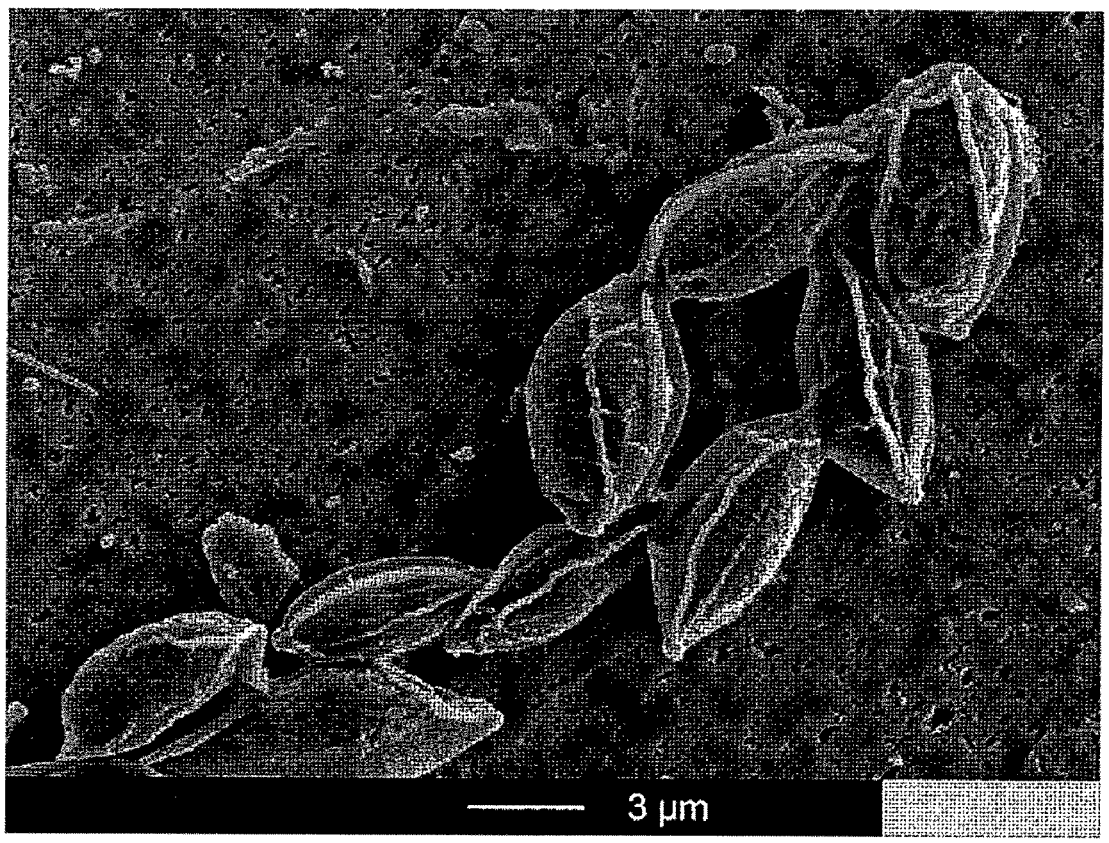
FIG. 1 shows an electron microscope image of the microalga *Scenedesmus almeriensis*.

The invention claimed is:

1. A biologically pure culture of *Scenedesmus almeriensis*, lutein producer, deposited within the Culture Collection of Algae and Protozoa (CCAP) under accession number CCAP 276/24.

2. The *Scenedesmus almeriensis* strain according to claim 1, wherein said strain grows in a temperature range between 10° C. and 40° C., preferably at 30° C.

3. The *Scenedesmus almeriensis* strain according to claim 1, wherein said strain grows in a pH range between 7.0 and 9.5, preferably at a pH of 8.0.

4. A method for nourishing fish hatchlings and mollusk larvae, comprising providing the microalgae *Scenedesmus almeriensis* of claim 1 to the fish hatchlings or mollusk larvae as a food.

5. A method for nourishing animals and livestock, comprising providing the microalgae *Scenedesmus almeriensis* of claim 1 to the animals or livestock as a food.

6. A dietary supplement comprising the microalgae *Scenedesmus almeriensis* of claim 1.

7. A method for obtaining oils rich in poly-unsaturated fatty acids, comprising cultivating the microalgae *Scenedesmus almeriensis* CCAP 276/24 according to claim 1 at a pH range of from 7.0 to 9.5 and a temperature range between 10° C. to 40° C., and isolating the oil rich in poly-unsaturated fatty acids from said microalgae.

8. A method for obtaining oils rich in carotenoids, comprising cultivating the microalgae *Scenedesmus almeriensis* CCAP 276/24 according to claim 1 at a pH range of from 7.0 to 9.5 and a temperature range between 10° C. to 40° C., and isolating the oil rich in carotenoids from said microalgae.

9. A process for obtaining an oil rich in lutein comprising cultivating the microalgae *Scenedesmus almeriensis* CCAP 276/24 according to claim 1 at a pH range of from 7.0 to 9.5 and a temperature range between 10° C. to 40° C., and isolating the oil rich in lutein from said microalgae.

* * * * *